United States Patent [19]

Raccach

[11] 4,407,828

[45] * Oct. 4, 1983

[54] FERMENTATION METHOD USING A SELECTED LACTOBACILLUS

[75] Inventor: Moshe Raccach, Tempe, Ariz.

[73] Assignee: Microlife Technics, Inc., Sarasota, Fla.

[*] Notice: The portion of the term of this patent subsequent to Dec. 1, 1998 has been disclaimed.

[21] Appl. No.: 268,354

[22] Filed: May 29, 1981

[51] Int. Cl.$^3$ .................... A23L 1/31; C12P 7/56; C12N 1/20; C12R 1/245

[52] U.S. Cl. .................... 426/56; 426/7; 426/9; 435/139; 435/253; 435/856

[58] Field of Search .................... 426/7, 9, 48, 55, 56, 426/59, 574; 435/139, 856, 253

[56] References Cited

U.S. PATENT DOCUMENTS

| | | | |
|---|---|---|---|
| 2,225,783 | 2/1940 | Jensen et al. | 99/109 |
| 2,945,766 | 7/1960 | Chaiet | 99/107 |
| 3,098,744 | 7/1963 | Von Lorch et al. | 99/1 |
| 3,193,391 | 6/1965 | Jansen et al. | 99/157 |
| 3,561,977 | 2/1971 | Rothchild | 99/109 |
| 3,814,817 | 6/1974 | Everson | 426/56 |
| 3,960,664 | 6/1976 | Olsen et al. | 195/59 |
| 3,984,575 | 10/1976 | Farr | 426/61 |
| 4,041,181 | 8/1977 | Burrows et al. | 426/55 |
| 4,160,038 | 7/1979 | Groben et al. | 426/56 |
| 4,303,679 | 12/1981 | Raccach | 426/59 |

OTHER PUBLICATIONS

Hanna, M. O. et al., Journal of Food Protection, vol. 43, pp. 837–841.
Bergey's Manual of Determinative Bacteriology, 8th ed., 1974, pp. 583 & 584.

Primary Examiner—Thomas G. Wiseman
Assistant Examiner—Elizabeth J. Curtin
Attorney, Agent, or Firm—Ian C. McLeod

[57] ABSTRACT

A method is described for producing fermented foods by generating lactic acid in the food using a culture of a lactobacillus similar to *Lactobacillus casei* subspecies *alactosus* NRRL-B-12,344 and a stimulatory food grade metal salt, wherein the culture has unique rapid low temperature fermentation characteristics and wherein lactose, glycogen, and starch are not fermented by the culture. The preferred *Lactobacillus casei* subspecies *alactosus* is NRRL-B-12,344 or strains having low temperature food fermentation characteristics in common with this strain. In order to provide rapid fermentation, the stimulatory, food grade metal salt, usually a manganese salt, is provided in the food or the culture which is added to the food with the selected lactobacillus to accelerate fermentation. The cultures are particularly suited for the controlled fermentation of carbohydrates, naturally present in or added to the food to provide a selected final pH.

11 Claims, No Drawings

FERMENTATION METHOD USING A SELECTED LACTOBACILLUS

BACKGROUND OF THE INVENTION

The present invention relates to a method for fermenting foods using selected cultures of a lactobacillus having the rapid low temperature fermentation characteristics of *Lactobacillus casei* subspecies *alactosus* NRRL-B-12,344 usually at food temperatures of between 15.6° C. (60° F.) and 26.7° C. (80° F.) in the presence of an effective amount of a stimulatory, food grade metal salt, preferably a manganese salt. Fermentation temperatures in the range between about 15.6° C. (60° F.) and 48.9° C. (120° F.) can be used; however, lower temperatures than 26.7° C. (80° F.) are preferred, particularly to reduce the risk of significant *Staphylococcus aureus* growth in fermented meats.

Prior Art

The prior art has generally described meat fermentation methods using many different cultures of lactobacilli which generate lactic acid from dextrose, lactose, glycogen, sucrose and/or starch in foods. U.S. Pat. Nos. 2,225,783 and 3,93,391 to Jensen et al.; 3,098,744 to Von Lorch et al; 3,814,817 to Everson et al. and 3,561,977 and 3,960,664 to Rothchild et al are representative of this prior art which is extensive. In this prior art, various strains of lactobacilli are described as useful for fermenting foods; however, these cultures have the characteristic of fermenting lactose, starch and glycogen which, when present in uncontrolled or unknown amounts in a meat mixture to be fermented, can result in the production of excessive amounts of lactic acid causing an undesirable low final pH in the fermented meat.

It is generally true of lactobacilli and specifically most strains of *Lactobacillus casei* that sausage fermentations proceed very slowly or not at all at temperatures less than 26.7° C. (80° F.). Commercially meat fermentations are usually conducted above 26.7° C. (80° F.) for this reason.

Usually semi-dry sausge is prepared by fermenting a carbohydrtae particularly dextrose and/or naturally occurring glycogen in meat in less than about 30 hours. Dry sausage is usually fermented over a period of at least two to three days. Both methods preferably involve a rapid initial fermentation which produces lactic cid in the meat thereby lowering the pH. Once the pH is lowered to the desired level any further lowering of the pH makes the product unacceptable. This can particularly occur during the drying period required to make dry sausage.

In general, the prior art strains of lactobacilli used for making sausge to develop a pH of less than about 5.0 in about 30 hours or less, require fermentation at an elevated temperature range between about 26.6° C. to 45° C. (80° F. to 113° F.). These lactobacilli are too slow at lower meat temperatures between about 10° C. to 26.7° (50° F. to 80° F.) since they take much longer to develop a pH of less than about 5.0.

In my prior application Ser. No. 114,760, now U.S. Pat. No. 4,303,679, I described the use of manganese salts in the fermentation of meats using specific unique strains of *Pediococcus pentosaceus*. U.S. Pat. No. 2,945,766 to Chiat generally describes the use of manganese salts in meat fermentations with lactobacilli at temperatures at or above 26.7° C. (80° F.).

Hanna, M.O., et al Journal of Food Protection Vol 43 pages 837–841 describe the use of *Lactobacillus casei* subspecies *alactosus* in vacuum packed meat at 1° to 3° C. for preservation without fermentation. These cultures were not effective and detracted from the taste of the meat.

OBJECTS

It is therefore an object of the present invention to provide a method for producing fermented foods using selected cultures of a lactobacillus similar to *Lactobacillus casei* subsp. *alactosus* NRRL-B-12,344 with a stimulatory metal salt which cultures ferment rapidly at low temperatures. It is particularly an object of the present invention to provide a method wherein fermented meats can be produced using the selected lactobacillus similar to *Lactobacillus casei* subsp. *alactosus* NRRL-B-12,344 and stimulatory metal salt wherein the meat mixture to be fermented contains unknown or uncontrolled amounts of certain carbohydrates. These and other objects will become increasingly apparent from the following description.

GENERAL DESCRIPTION

The present invention relates to the improvement in a food fermentation method including the steps of providing lactic acid producing bacteria in the food with an assimilable carbohydrate and then fermenting the food with the bacteria so that lactic acid is produced from the carbohydrate over a period of time in the food which comprises: providing in admixture in a food a culture of a lactobacillus with an assimilable carbohydrate and with a stimulatory, food grade metal salt in an amount sufficient to accelerate the fermentation by the lactobacillus, wherein the culture is characterized by having low temperature fermentation characteristics in food at least as rapid as *Lactobacillus casei* subspecies *alactosus* NRRL-B-12,344; and fermenting the food admixture at temperatures between about 15.6° C. and 48.9° C. so that lactic acid is produced in the food product. Using *Lactobacillus casei* subsp. *alactosus* NRRL-B-12,344, a pH of 5.0 is achieved at 24° C. in less than about 24 hours with an initial food pH of about 5.9 without the metal salt. With the metal salt, the fermentation time is significantly decreased under equivalent conditions.

The present invention particularly relates to the meat fermentation method including the steps of providing lactic acid producing bacteria in the meat with an assimilable sugar and then fermenting the meat with the bacteria so that lactic acid is produced from the sugar over a period of time in the fermented meat wherein the improvement comprises: providing in admixture in meat a culture of a lactobacillus having low temperature meat fermentation characteristics at least as rapid as *Lactobacillus casei* subspecies *alactosus* NRRL-B-12,344 at a concentration of between about $10^5$ and $10^9$ of the lactobacillus per gram of met with an assimilable carbohydrate and with a stimulatory food grade manganese salt in an amount sufficient to stimulate the growth of the lactobacillus wherein the lactobacillus culture is characterized by an ability to rapidly ferment in the meat admixture at meat temperatures of about 24° C. to produce a pH of about 5 or less; and fermenting the meat admixture at smokehouse temperatures between about 15.6° C. and 48.9° C. so that lactic acid is produced in the fermented meat product.

The present invention further relates to a culture of lactobacillus adapted for meat fermentations including an assimilable carbohydrate at smokehouse temperatures between about 15.6° C. and 48.9° C. which comprises a selected lactobacillus grown in growth medium including assimilable sources of carbon, nitrogen and inorganic substances to a concentration of at least about $1 \times 10^7$ of the lactobacillus per ml, having a pH between about 4 and 8 and containing a stimulatory food grade metal salt after growth in an amount sufficient to accelerate the fermentation in the meat by providing a concentration of metal ion between about 0.01 ppm and 1500 ppm in the meat, wherein the selected lactobacillus culture is characterized by an ability to rapidly ferment in a meat admixture with an assimilable sugar at temperatures of about 24° C. to produce a pH less than about 5 at least as rapidly as *Lactobacillus casei* subsp. *alactosus* NRRL-B-12,344.

The preferred selected *Lactobacillus casei* subsp. *alactosus* strain of the present invention has been deposited at the Northern Regional Research Laboratory of the USDA, Peoria, Ill. and was designated as NRRL-B-12,344. NRRL-B-12,344 or a lactobacillus which has substantially the same low temperature meat fermentation characteristics is used in the present invention. The essential identification characteristics of this strain and related strains are shown in Table I.

TABLE I

| Carbohydrate Fermentation Pattern | |
|---|---|
| Substrate | Fermentation Reaction |
| Adonitol | Negative |
| Arabinose | Negative |
| Cellobiose | Negative |
| Dextrose | Positive |
| Dulcitol | Negative |
| Galactose | Positive |
| Glycerol | Negative |
| Inositol | Negative |
| Lactose | Negative |
| Maltose | Positive |
| Mannitol | Negative |
| Mannose | Positive |
| Melibiose | Negative |
| Nitrate reductase | Negative |
| ONPG | Negative |
| Raffinose | Negative |
| Rhamnose | Negative |
| Salicin | Negative |
| Sorbitol | Weak + |
| Sucrose | Positive |
| Trehalose | Negative |
| Xylose | Negative |
| Starch | Negative |
| Esculin | Negative |
| Levulose | Positive |
| Amygdalin | Weak ± |
| Fructose | Positive |
| Gluconate | Positive |
| Glycogen | Negative |
| Ribose | Positive |
| Catalase | Negative |

Growth at 17° C., 24° C., 35° C. and no growth at 45° C. Produces primarily L(+) lactic acid. Acid but no gas from glucose. Acid and gas are produced from gluconate. *lactobacillus casei* subspecies *alactosus* has been used without a stimulatory metal salt at elevated temperatures above 26.7° C. (80° F.) in a mixed bacterial cultures with other lactic acid producing bacteria which broadly ferment most carbohydrates.

By a process which involves selective testing or genetic manipulation, lactobacillus having similar low temperature fermentation characteristics can be found or produced. In some instances the selected lactobacillus may not be of the same strain or the same species. All of this is well known to those skilled in the art.

The lactobacillus cells can be used as a concentrate having a pH between about 4 and 8 containing at least about $1 \times 10^7$ cells per gram up to about $10^{15}$ cells per gram, usually between about $1 \times 10^9$ and $10^{12}$ cells per gram, mixed with the stimulatory metal salt, preferably a manganese salt. The concentrates containing the stimulatory metal salt can be frozen with or without a freezing stabilizing agent such as monosodium glutamate, malt extract, non-fat dry milk, alkali metal glycerophosphate, glutamic acid, cystine, glycerol, or dextran or the like and then thawed for use or it can be lyophilized to a powder as is well known to those skilled in the art. The bacterial cells are used in a range between about $10^5$ to $10^9$ cells per gram of meat.

The stimulatory metal salt is used in an amount of metal cation in the salt above about 0.01 parts per million to about 1,500 parts per million by weight of the food to be fermented, preferably between about 0.1 and 100 ppm. The metal salt must be food grade. Such salts include for instance: manganese chloride, manganese sulfate, manganese citrate, manganese glycerophosphate, manganese oxide and manganese gluconate and various non-toxic metal salts of acids which are at least slightly soluble in water. Other metal salts include ferrous, ferric, magnesium calcium, zinc salts; however, none are as effective as manganese. The metal salt can be incorporated into the bacterial culture in an amount between about 0.01 and 50 percent by weight of the culture in order to provide the required amount of the metal salt needed in the food when the culture is added.

The low temperature lactobacillus, particularly NRRL-B-12,344, admixed with the stimulatory metal salt causes nitrile reduction due to the lowering of the pH of the meat in fermented metas, particularly pork including bacon and ham at a pH of between about 5 and 6 and at a concentration of bacteria between about $10^5$ and $10^{10}$ cells per ml. Usually the bacteria are included in the aqueous pickling solution and added to the meat as a spray or injected in an amount up to 15% by weight of the meat. Bacon is usually not reduced to a pH less than about 6 from an initial pH of 6.3 to 6.4. The lactobacillus with a stimulatory metal salt can lower the pH thus causing the nitrite reduction at lower temperatures than can be achieved in the absence of the stimulatory metal salt.

SPECIFIC DESCRIPTION

EXAMPLE 1

The preparation of the bacterial concentrate is described in this example. *Lactobacillus casei* subspecies *alactosus* NRRL-B-12,344 was grown in a growth medium such as described in U.S. Pat. Nos. 3,561,977 and 3,960,664. The medium includes a carbohydrate (glucose or other assimilable sugar) a nitrogen source (yeast extract or other source of amino acids) and traces of essential minerals or inorganic substances usually including a manganese salt (manganese sulfate monohydrate). The pH of the medium was initially adjusted to between 6.5 to 6.7 and the fermenter was set to maintain a pH of 6.0 during growth by the intermittent addition of ammonia. NRRL-B-12,344 was grown at 35° C. for about 15 hours. The bacteria were then concentrated using a centrifuge and, where the concentrate was not to be used immediately, were mixed with glycerin as a freezing stabilizing agent (10% by weight) and frozen for storage. The concentrates were also mixed with the manganese sulfate monohydrate as indicated in the following Examples prior to freezing. Freezing was less expensive than lyophilization and thus was preferred.

EXAMPLE 2

The *Lactobacillus casei* subspecies *alactosus* NRRL-B-12,344 culture of Example 1 prior to centrifugation contained $8 \times 10^9$ cells per milliliter in the growth medium. The culture was centrifuged and then resuspended at the rate of 5 milliliters of supernatant liquid per 100 ml of original culture. One milliliter (1 ml) of this concentrate was diluted with 20.3 milliliters of tap water and was inoculated at a rate of 4.5 milliliters of diluted culture per 0.93 kg (2.5 pounds) of sausage mix (40% pork and 60% beef with 3.0% salt, 1.0% dextrose, spices and 0.0156% sodium nitrite) which supplied about $3 \times 10^7$ cells per gram of the sausage mix. *Lactobacillus casei* subspecies *alactosus* NRRL-B-12,344 was tested with no metal ion, with calcium chloride and with manganese sulfate monohydrate in an amount of 13 parts per million of the metal cation based upon the weight of the sausage.

PROCEDURE (1) The meat was comminuted to the selected size.
(2) The dextrose, salt, spice mix, metal salt and sodium nitrite were added to the comminuted meat and mixed.
(3) The sausage mix was divided into aliquots and inoculated with appropriate cultures and mixed thoroughly.
(4) The sausage mix was stuffed into 53 mm diameter fibrous casings using a hydraulic stuffer.
(5) The sausages were fermented at 24° C. (75.2° F.) dry bulb and 21° C. (69.8° F.) wet bulb (80% room humidity) using a controlled environment chamber.

DETERMINATION OF pH (1) The pH of the sausage was determined at various times.
(2) Thirty grams of sausage were blended with 90 ml distilled water for 30 to 60 seconds. The pH of the slurry was determined. Piror to each pH reading, the pH meter was calibrated against two standard buffers (pH values of 7.00 and 4.01).

RESULTS

TABLE II

| Treatment *Lactobacillus casei* subsp. *alactosus* NRRL-B-12,344 | Fermentation Period (Hours) | | | | | | | | |
|---|---|---|---|---|---|---|---|---|---|
| | 0 | 13 | 15 | 17 | 18 | 19 | 20 | 22 | 23 |
| Control (no additive) | 5.87 | 5.59 | 5.52 | 5.35 | — | — | 5.19 | 5.13 | 5.06 |
| Ca chloride | 5.81 | 5.56 | 5.44 | 5.29 | — | — | 5.17 | 5.10 | 5.01 |
| Mn sulfate monohydrate | 5.86 | 5.51 | 5.29 | 5.15 | 5.06 | 4.97 | — | — | — |

Thus *Lactobacillus casei* subsp. *alactosus* NRRL-B-12,344 achieved a pH of less than 5.0 in less than 19 hours with the manganese salt as compared to more than 23 hours for the control. At this level, it cannot be said that calcium is significantly stimulatory.

COMPARATIVE EXAMPLE 3

Example 2 was repeated at 13 ppm metal ion concentration except that *Lactobacillus lactis*, Farr (NRRL-B-4528) and *Lactobacillus plantarum* (NRRL-B-5461) as described in U.S. Pat. Nos. 3,984,575 and 3,814,817 were used at 24° C. (75.2° F.). The results are shown in Table III.

TABLE III

| Treatment | Fermentation Period (Hours) | | | | | | | | | |
|---|---|---|---|---|---|---|---|---|---|---|
| | 0 | 21 | 24 | 27 | 29 | 34 | 38 | 45 | 48 | 51 |
| | | | | | (pH values) | | | | | |
| *Lactobacillus plantarum* NRRL-B-5461 | | | | | | | | | | |
| Control (no additive) | 5.80 | 5.62 | 5.53 | 5.20 | 5.11 | — | — | — | | |
| CaCl$_2$ | 5.19 | 5.65 | 5.51 | 5.24 | 5.13 | — | — | — | | |
| MnSO$_4$ monohydrate | 5.77 | 5.56 | 5.33 | 5.00 | — | — | — | — | | |
| *Lactobacillus lactis* Farr NRRL-B-5628 | | | | | | | | | | |
| Control (no additive) | 5.86 | 5.79 | 5.72 | 5.73 | — | 5.59 | 5.39 | 5.20 | 5.19 | 5.15 |
| CaCl$_2$ | 5.81 | 5.80 | 5.75 | 5.73 | — | 5.58 | 5.35 | 5.23 | 5.16 | 5.15 |
| MnSO$_4$ Monohydrate | 5.88 | 5.80 | 5.80 | 5.77 | — | 5.48 | 5.24 | 5.03 | — | — |

COMPARATIVE EXAMPLE 4

Example 2 was repeated with *Lactobacillus casei* NRRL-B-12428, which has higher teperature fermentation characteristics, at the level of $3 \times 10^7$ cells per gram of sausage and at 24° C. (75.2° F.). The result was that the fermentation was very long (40 hours) and there appeared to be only a slight improved result over the control. The results are shown in Table IV where pH is shown as a function of time.

TABLE IV

| Treatment | Initial | Fermentation Period (Hours) | | | | | |
|---|---|---|---|---|---|---|---|
| | | 16 | 19 | 23 | 25 | 40 | 44 |
| Control (no additive) | 5.76 | 5.67 | 5.69 | 5.52 | 5.56 | 5.16 | 4.98 |
| CaCl$_2$ | 5.76 | 5.65 | 5.65 | 5.64 | 5.61 | 5.16 | 4.99 |
| MnSO$_4$ monohydrate | 5.75 | 5.71 | 5.67 | 5.63 | 5.59 | 4.84 | — |

| Final Viable Counts | |
|---|---|
| Control | $36 \times 10^7$ |
| MnSO$_4$ monohydrate | $40 \times 10^7$ |
| CaCl$_2$ | $34 \times 10^7$ |

Comparative Example 4 shows the metal salts are only selectively stimulatory at low temperatures even with certain strains of *Lactobacillus casei.*

Lactobacillus species having low temperature fermentation characteristics as rapid as *Lactobacillus casei* subspecies *alactosus* NRRL-B-12,344 with a stimulatory metal salt provides a significantly improved method for fermenting foods, vegetables and meats.

I claim:

1. In a food fermentation method including the steps of providing lactic acid producing bacteria in the food with an assimilable carbohydrate and then fermenting the food with the bacteria so that lactic acid is produced from the carbohydrate over a period of time in the food the improvement which comprises:
   (a) providing in admixture in a food a culture of a lactobacillus with an assimilable carbohydrate and with a stimulatory, food grade metal salt in an amount sufficient to accelerate the fermentation by the lactobacillus, wherein the culture is characterized by having low temperature fermentation characteristics in food at least as rapid as *Lactobacillus casei* subspecies *alactosus* NRRL-B-12,344; and
   (b) fermenting the food admixture at temperatures between about 15.6° C. and 48.9° C. so that lactic acid is produced in the food product.

2. In a meat fermentation method including the steps of providing lactic acid producing bacteria in the meat with an assimilable sugar and then fermenting the meat with the bacteria so that lactic acid is produced from the sugar over a period of time in the fermented meat the improvement which comprises:
   (a) providing in admixture in meat a culture of a selected lactobacillus having low temperature meat fermentation characteristics at least as rapid as *Lactobacillus casei* subspecies *alactosus* NRRL-B-12,344 at a concentration of between about $10^5$ and $10^9$ of the selected lactobacillus per gram of meat with an assimilable carbohydrate and with a stimulatory, food grade manganese salt in an amount sufficient to stimulate the growth of the lactobacillus, wherein the lactobacillus culture is characterized by an ability to rapidly ferment in the meat admixture at meat temperatures of about 24° C. to produce a pH of about 5 or less and
   (b) fermenting the meat admixture at smokehouse temperatures between about 15.6√ C. and 48.9° C. so that lactic acid is produced in the fermented meat product.

3. The method of claim 2 wherein the meat admixture contains a food grade nitrite as a preservative which is partially reduced due to the lactic acid produced by the lactobacillus.

4. The method of claim 2 wherein the lactobacillus, sugar, preservatives and metal salt are added to the meat as an aqueous pickling solution containing between about $10^5$ to $10^{10}$ of the lactobacillus per ml in an amount of the pickling solution up to about 15 percent by weight based upon the meat weight and wherein the meat is held at 21.1° C. to 38° C. until a pH between about 5 and 6 is achieved.

5. The method of claim 1 or 2 wherein the manganese salt is manganese sulfate and wherein the food is fermented at temperatures of 26.7° C. or less to produce a pH of less than about 5.

6. The method of claim 1 or 2 wherein the lactobacillus has essentially the same meat fermentation characteristics as NRRL-B-12,344.

7. The method of claim 1 or 2 wherein the lactobacillus is *Lactobacillus casei* subspecies *alactosus* NRRL-B-12,344.

8. The method of claim 1 or 2 wherein the lactobacillus has been grown in the presence of a manganese salt and further manganese salt is added to the culture as the metal salt after growth and wherein the lactobacillus is admixed with the food as a liquid concentrate containing at least about $10^7$ cells per gram.

9. The method of claim 8 wherein the bacterial concentrate is frozen with the manganese salt prior to use and thawed to provide a liquid concentrate for admixture with the food.

10. The method of claim 1 or 2 wherein the lactobacillus is in a lyophilized, powdered form containing the manganese salt which is provided in the food as a powder.

11. The method of claim 1 wherein portions of fermented food are utilized as a source of lactobacillus for a subsequent food fermentation with the metal salt.

* * * * *

UNITED STATES PATENT AND TRADEMARK OFFICE
CERTIFICATE OF CORRECTION

PATENT NO. : 4,407,828
DATED : 1983 October 4
INVENTOR(S) : Moshe Raccach

It is certified that error appears in the above-identified patent and that said Letters Patent are hereby corrected as shown below:

```
Column 1, line 27 "3,93,391" should be --3,193,391--.

Column 1, line 50 "cid" should be --acid--.

Column 1, line 56 "sausge" should be --sausage--.

Column 2, line 57 "met" should be --meat--.

Column 3, line 63 delete "a".

Column 4, line 35 "nitrile" should be --nitrite--.

Column 4, line 36 "metas" should be --meats--.

Column 6, line 9 "Piror" should be --Prior--.

Column 6, line 34 "4528" should be --5628--.

Column 6, line 62 "teperature" should be --temperature--.

Column 8, line 10 "√" should be --°--.
```

Signed and Sealed this

Third Day of April 1984

[SEAL]

Attest:

GERALD J. MOSSINGHOFF

Attesting Officer   Commissioner of Patents and Trademarks